(12) United States Patent
Gliner

(10) Patent No.: US 6,701,190 B2
(45) Date of Patent: Mar. 2, 2004

(54) SYSTEM AND METHOD FOR VARYING CHARACTERISTICS OF ELECTRICAL THERAPY

(75) Inventor: Brad Gliner, Sammamish, WA (US)

(73) Assignee: Meagan Medical, Inc., Reno, NV (US)

( * ) Notice: Subject to any disclaimer, the term of this patent is extended or adjusted under 35 U.S.C. 154(b) by 262 days.

(21) Appl. No.: 09/751,503

(22) Filed: Dec. 29, 2000

(65) Prior Publication Data

US 2002/0055762 A1 May 9, 2002

Related U.S. Application Data

(63) Continuation-in-part of application No. 09/686,993, filed on Oct. 10, 2000.

(51) Int. Cl.[7] ............................................. A61N 1/08
(52) U.S. Cl. ......................................... 607/62; 607/46
(58) Field of Search ........................ 607/46, 66, 69–74, 607/48, 50–52, 62

(56) References Cited

U.S. PATENT DOCUMENTS

| | | | |
|---|---|---|---|
| 4,256,116 A | 3/1981 | Meretsky et al. | |
| 4,262,672 A | 4/1981 | Kief | |
| 4,381,012 A | 4/1983 | Russek | |

(List continued on next page.)

OTHER PUBLICATIONS

U.S. patent application Ser. No. 09/667,183, Leonard, filed Sep. 21, 2000.
U.S. patent application Ser. No. 09/751,382, Bishay et al., filed Dec. 29, 2000.
U.S. patent application Ser. No. 29/130,210, Leonard et al., filed Sep. 28, 2000.
U.S. patent application Ser. No. 29/134,817, Bishay et al., filed Dec. 29, 2000.
*Association For Advancement Of Medical Instrumentation, "Implantable Peripheral Nerve Stimulators," American National Standard, ANSI/AAMI NS15—1995 pp. 1–8.
*Almay, B.G.L. et al., "Long–Term High Frequency Transcutaneous Electrical Nerve Stimulation (hi–TNS) in Chronic Pain. Clinical Response and Effects on CSF-Endorphins, Monoamine Metabolites, Substance P–Like Immunoreactivity (SPLI) and Pain Measures," Journal of Psychosomatic Research, (1985) vol. 29, No. 3, pp. 247–257, Pergamon Press Ltd. Great Britain.
*Baker, L. L., et al. "Effects of Waveform on Comfort during Neuromuscular Electrical Stimulation," Clinical Orthopaedics and Related Research, Aug. 1998, No. 223, pp. 75–85.
*Balogun, J. et al., "Effects of Ramp Time on Sensory, Motor and Tolerance Thresholds during Exogenous Electrical Stimulation," The Journal of Sports Medicine and Physical Fitness, (Dec. 1991) vol. 31, No. 4, pp. 521–526.

(List continued on next page.)

Primary Examiner—George R. Evanisko
(74) Attorney, Agent, or Firm—Blank Rome, LLP

(57) ABSTRACT

A system and method for providing percutaneous electrical nerve stimulation therapy to a patient. A method in accordance with one embodiment to the invention can include coupling an electrode to the recipient, applying electrical pulses to the probe, and varying a characteristic of the pulses applied to the recipient. For example, the pulses can be automatically varied from a value of no more than about 4 Hz to a value of no less than about 10 Hz and back over a period of greater than 6 seconds. The frequency variation can be repeated for a number of periods during the course of a session, or the frequency characteristics can change with subsequent periods. Characteristics of the electrical pulses can be changed depending on the duration of the session. The method for varying characteristics of the electrical pulses can be automatically implemented by a computer.

5 Claims, 10 Drawing Sheets

U.S. PATENT DOCUMENTS

| | | | |
|---|---|---|---|
| 4,408,617 A | 10/1983 | Auguste | |
| 4,431,000 A | 2/1984 | Butler et al. | |
| 4,541,432 A | 9/1985 | Molina-Negro et al. | |
| 4,556,064 A | 12/1985 | Pomeranz et al. | |
| 4,712,558 A | 12/1987 | Kidd et al. | |
| 5,702,359 A | 12/1997 | Hofmann et al. | |
| 5,873,849 A | 2/1999 | Bernard | |
| 5,891,182 A * | 4/1999 | Fleming | 607/50 |
| 5,968,011 A | 10/1999 | Larsen et al. | |
| 6,021,353 A * | 2/2000 | Wang | 607/72 |
| 6,035,236 A | 3/2000 | Jarding et al. | |
| 6,117,077 A | 9/2000 | Del Mar et al. | |
| 6,212,432 B1 * | 4/2001 | Matsuura | 607/76 |
| 6,236,890 B1 * | 5/2001 | Oldham | 607/68 |
| 6,355,021 B1 | 3/2002 | Nielsen et al. | |

OTHER PUBLICATIONS

*Brull, S. J., et al., "Pulse Width, Stimulus Intensity, Electrode Placement, and Polarity during Assessment of Neuromuscular Block," Anesthesiology, (Oct. 1995) V. 83, No. 4, pp. 702–709, Lippincott–Raven Publishers.

*Cassuto, J. et al., "The Use of Modulated Energy Carried on a High Frequency Wave for the Relief of Intractable Pain," International Journal of Clinical Pharm. Research 91993) XIII (4) pp. 239–241.

*Cramp, A.F.L. et al., "The Effect of High–and Low–Frequency Transcutaneous Electrical Nerve Stimulation Upon Cutaneous Blood Flow and Skin Temperature in Healthy Subjects," Clinical Physiology 20, (2000) 2, pp. 150–157, Blackwell Science Ltd.

*Empi EPIX XL TENS Instruction Manual, Empi. Inc. (Sep. 1998) U.S. Patent No. D319, 881, 2 pages.

*Foster, N.E., et al., "Manipulation of Transcutaneous Electrical Nerve Stimulation Variables Has No Effect on Two Models of Experimental Pain in Humans," The Clinical Journal of Pain, (1996) 12; pp. 301–310, Lippincott–Raven Publishers, Philadelphia.

*Galleti, S.P., et al., "Highlights in the Subject of Low Frequency–High Intensity TENS," Minerva Stomatologica (Italy) (Sep. 1995), 44, pp. 421–429 (Summary in English Only).

*Ghoname, E. et al. "The Effect of Stimulus Frequency on the Analgesic Response to Percutaneous Electrical Nerve Stimulation in Patients with Chronic Low Back Pain", Anesthesia & Analgesia (Oct. 1999) 88: 841–6.

*Gopalkrishnan, P., et al., "Effect of Varying Frequency, Intensity, and Pulse Duration of Transcutaneous Electrical Nerve Stimulation on Primary Hyperalgesia in Inflamed Rats," Arch. Phys. Med. Rehabil., (Jul. 2000) vol. 81, pp. 984–990.

*Gracanin, F., et al., "Optimal Stimulus Parameters for Minimum Pain in the Chronic Stimulation of Innervated Muscle," Arch. Phys. Med. Rehabil. (Jun. 1975) vol. 56, pp. 243–249.

*Hazma, M.A., et al., "Effect of the Frequency of Transcutaneous Electrical Nerve Stimulation on the Postoperative Opioid Angalgesic Requirement and Recovery Profile," Anesthesiology, (Nov. 1999) V. 91, No. 5, pp. 1232–1238.

*Han, J.S. et al., "Effect of Low–and High–Frequency TENS on Met–enkephalin–Arg–Phe and dynorphin A immunoreactivity in human lumbar CSF," Pain, (1991) vol. 47, pp. 295–298, Elsevier Science Publishers B.V.

*Jette, D. U. et al., "Effect of Different Forms of Transcutaneous Electrical Nerve Stimulation on Experimental Pain," Physical Therapy, (Feb. 1986) vol. 66/No. 2, pp. 187–193.

*Johnson M. I. et al., "Analgesic Effects of Different Pulse Patterns of Transcutaneous Electrical Nerve Stimulation on Cold–Induced Pain in Normal Subjects," Journal of Psychosomatic Research (1991) vol. 35, No. 2/3, pp. 313–321, Great Britain.

*Johnson, M. I. et al., "Analgesic Effects of Different Frequencies of Transcutaneous Electrical Nerve Stimulation on Cold–Induced Pain in Normal Subjects," Pain, (1989) 39, pp. 231–236, Elsevier Science Publishers B.V.

*Johnson, M.I. et al., "An In–Depth Study of Long–Term Users of Transcutaneous Electrical Nerve Stimulation (TENS). Implications for Clinical Use of TENS," Pain (1991) 4, pp. 221–229, Elsevier Science Publishers B.V.

*Katims, J.J. et al., "Transcutaneous Nerve Stimulation Frequency and Waveform Specificity in Humans," Appl. Neurophysiol. (1986) 49: pp. 86–91.

*Leem, J.W. et al., "Electrophysiological Evidence for the Antinociceptive Effect of Transcutaneous Electrical Stimulation on Mechanically Evoked Responsiveness of Dorsal Horms Neurons in Neuropathic Rats," Neuroscience Letters (1995) 192, pp. 197–200, Elsevier Science Ireland Ltd.

*Liss, S. et al., "Physiological and Therapeutic Effects of High Frequency Electrical Pulses," Integrative Physiological and Behavioral Science, (Apr.–Jun. 1996) vol. 31, No. 2, pp. 88–94.

*Marchand, S. et al., "Modulation of Heat Pain Perception by High Frequency Transcutaneous Electrical Nerve Stimulation (TENS)," The Clinical Journal of Pain (1991) 7: pp. 122–129, Raven Press Ltd., New York.

*Moreno–Aranda, J. et al., "Electrical Parameters for Over–the–Skin Muscle Stimulation," J. Biomechanics, (1981) vol. 14, No. 9, pp. 579–585, Pergamon Press Ltd.

*Moreno–Aranda, J. et al., "Investigation of Over–the–Skin Electrical Stimulation Parameters for Different Normal Muscles and Subjects," J. Biomechanics, (1981) vol. 14, No. 9, pp. 587–593, Pergamon Press Ltd., Great Britain.

*O'Brien, W. J. et al., "Effect of Transcutaneous Electrical Nerve Stimulation on Human Blood B–Endorphin Levels," Physical Therapy, (Sep. 1984) vol. 64/No. 9, pp. 1367–1374.

*Omura, Y., "Basic Electrical Parameters for Safe and Effective Electro–Therapeutics [Electro–Acupuncture, TES, TENMS, (or TEMS), TENS and Electro–Magnetic Field Stimulation with or without Drug Field] for Pain, Neuromuscular Skeletal Problems, and Circulatory Disturbances," Acupuncture & Electro–Therapeutics Res., Int. J. (1987) vol. 12, pp. 201–225, Pergamon Journals Ltd., USA.

*Ordog, G.J., "Transcutaneous Electrical Nerve Stimulation versus Oral Analgesic: A Randomized Double–Blind Controlled Study in Acute Traumatic Pain," American Journal of Emergency Medicine, (Jan. 1987) vol. 5, No. 1, pp. 6–10.

*Romita, V.V. et al., "Parametric Studies on Electroacupuncture–Like Stimulation in a Rat Model; Effects of Intensity, Frequency, and Duration of Stimulation on Evoked Antinociception," Brain Research Bulletin, (1997) vol. 42, No. 4, pp. 289–296, Elsevier Science Inc., USA.

*Sluka, K.A. et al., "Treatment with either High or Low Frequency TENS Reduces the Secondary Hyperalgesia Observed After Injection of Kaolin and Carrageenan into the Knee Joint," Pain, (1998) 77, pp. 97–102, Elsevier Science B.V.

*Starobinets, M. et al., "Analgesic Effect of High–Frequency and Acupuncture–Like Transcutaneous Electric Stimulation of Nerve Fibers in Spinal Osteochondrosis," (Russian) Zhurnal Nevropatologii I Psikhiatrii Imeni S.S. Korsakova (1985) 85, (3) pp. 350–354.

*Van Doren, C.L., "Contours of Equal Perceived Amplitude and Equal Perceived Frequency for Electrocutaneous Stimuli," Perception and Psychophysics (1997) 59, (4), pp. 613–622.

* cited by examiner

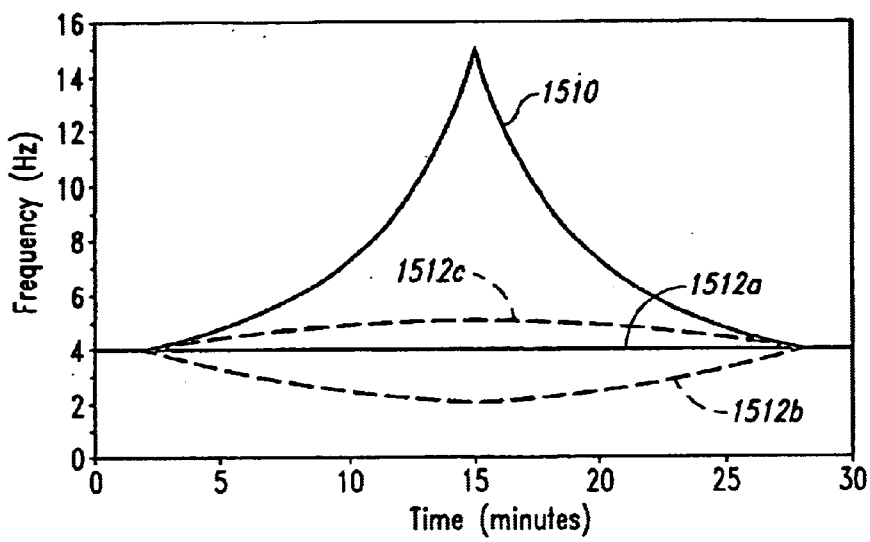
*Fig. 15*
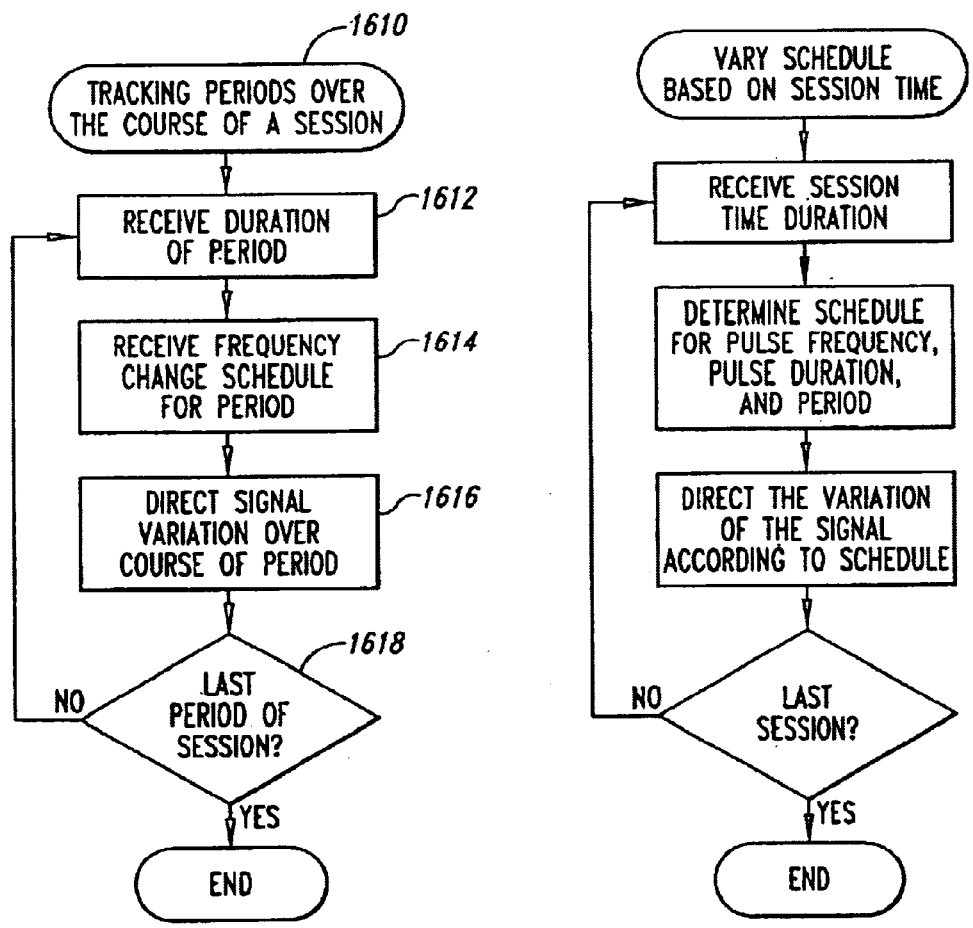
*Fig. 16*          *Fig. 17*

SYSTEM AND METHOD FOR VARYING CHARACTERISTICS OF ELECTRICAL THERAPY

CROSS-REFERENCE TO RELATED APPLICATIONS

The present application is a continuation-in-part of U.S. application Ser. No. 09/686,993, titled "System and Method for Providing Percutaneous Electrical Therapy," filed Oct. 10, 2000 and incorporated herein in its entirety by reference.

FIELD OF THE INVENTION

The present invention is generally directed to a system and method for varying characteristics of electrical signals for nerve stimulation therapy.

BACKGROUND

Electrical therapy has long been used in medicine to treat pain and other conditions. One such therapy is transcutaneous electrical nerve stimulation (TENS). This therapy involves the delivery of electrical energy through patch electrodes placed on the surface of a patient's skin to treat pain in tissue beneath and around the location of the patch electrodes. The electrical energy is typically delivered to the patient in a waveform that varies according to a single preset frequency or a limited frequency combination. For example, some conventional TENS devices can provide a signal that oscillates in a single step between a high frequency and a low frequency.

The relationship between waveform frequency and efficacy varies from patient to patient and from condition to condition. Previous art TENS studies therefore vary greatly in their conclusions regarding the efficacy of different TENS waveforms. For example, a review of 46 published TENS studies showed a wide variation in pain relief effect. It is difficult (if not impossible) to determine from these studies which waveform frequency should be used to treat a new patient or a prior patient with a new condition.

Some studies have attempted to determine the relationship between waveform frequency and the mechanism underlying the therapeutic effect, such as pain relief. For example, one study of 37 patients determined that TENS applied at a relatively low frequency (2 Hz) increased the concentration of an enkaphalin pain reliever in patients' cerebral spinal fluid (CSF), while TENS applied at a relatively high frequency (100 Hz) increased the concentration of a dynorphin pain reliever in the CSF. These studies did not attempt to correlate the increased concentrations of these substances in the CSF with pain relief effect, nor did they suggest which patients would benefit more from one frequency or the other or which conditions were best treated at one frequency or the other.

Electrical therapy to treat pain and other conditions may also be delivered percutaneously. This percutaneous approach is commonly referred to as Percutaneous Neuromodulation Therapy (PNT) or Percutaneous Electrical Nerve Stimulation (PENS). Like the TENS studies, however, published studies describing percutaneous electrical therapy have focused on limited patient populations and on limited frequencies and frequency combinations. These studies do not guide clinicians in the treatment of any particular patient with unknown electrical therapy response characteristics and an unknown condition underlying the apparent symptoms.

Thus, a significant drawback of conventional electrical therapy approaches is that they fail to provide a therapeutic regime that will be efficacious across entire populations of patients and across a variety of patient conditions. For example, some conventional approaches require trial and error testing of the patient to determine which waveform frequency would be best to treat that patient's condition, thereby consuming scarce medical personnel time and delaying the possible therapeutic effect for the patient. Furthermore, conventional electrical therapy systems take a "one size fits all" treatment approach with widely varying results.

SUMMARY

The present invention is directed toward methods and systems for delivering electrical therapy to a recipient. In one aspect of the invention, the method can include coupling an electrode (such as a percutaneous probe) to the recipient and applying electrical pulses to the electrode. The method can further include varying a frequency of the electrical pulses from a first value of no more than about 4 Hz to a second value of no less than about 10 Hz and back to the first value over a period of time greater than 6 seconds. The frequency of the electrical pulses can be automatically varied and, in a further aspect of the invention, can be automatically varied in response to a signal received from the recipient. The method can further include varying a frequency of the electrical pulses over a first range of frequencies for a first period of time greater than 6 seconds, and varying the frequency over a second period of a time approximately the same as the first period of time. The frequency of the electrical signal pulses can be varied over the course of a session having a duration of from about 20 minutes to about 45 minutes.

In another aspect of the invention, the method can include selecting a first session time for applying a first electrical signal to an electrode coupled to a recipient. The method can further include applying pulses of the first electrical signal according to a first schedule for pulse frequency, duration and period. The method can further include selecting a second session time different than the first session time and applying pulses of a second electrical signal according to a second schedule. The manner in which at least one of the frequency, duration and period varies during the second schedule is based on the second session time and is different for the second schedule than for the first schedule.

Another aspect of the invention is directed toward a computer-implemented method for controlling administration of electrical therapy to a recipient. The method can include receiving an indication of an initiation of a therapy session and receiving a schedule for varying a frequency of electrical pulses as a function of time. The method can further include directing a variation of a frequency with which electrical pulses are applied to an electrode according to the schedule while the electrode is coupled to the recipient. The method can further include receiving an indication of an end of the therapy session, and directing the electrical pulses to cease. The schedule can be retrieved from a computer-readable medium and can include a first frequency value of no more than about 4 Hz, a second frequency value of no less than about 10 Hz, and a time period value. Directing a variation of the frequency can include directing a frequency of the electrical pulses to vary from the first frequency value to the second frequency value during the time period.

BRIEF DESCRIPTION OF THE DRAWINGS

FIG. 15 is a plot illustrating a schedule for varying the difference between a minimum frequency and a maximum frequency with which electrical pulses are administered over the course of a therapy session in accordance with another embodiment of the invention.

FIG. 16 is a flow diagram illustrating a process for changing the duration of periods during a therapy session in accordance with still another embodiment of the invention.

FIG. 17 is a flow diagram illustrating a process for varying the characteristics of a schedule on the basis of session time, in accordance with still another embodiment of the invention.

DETAILED DESCRIPTION

Figure 1:
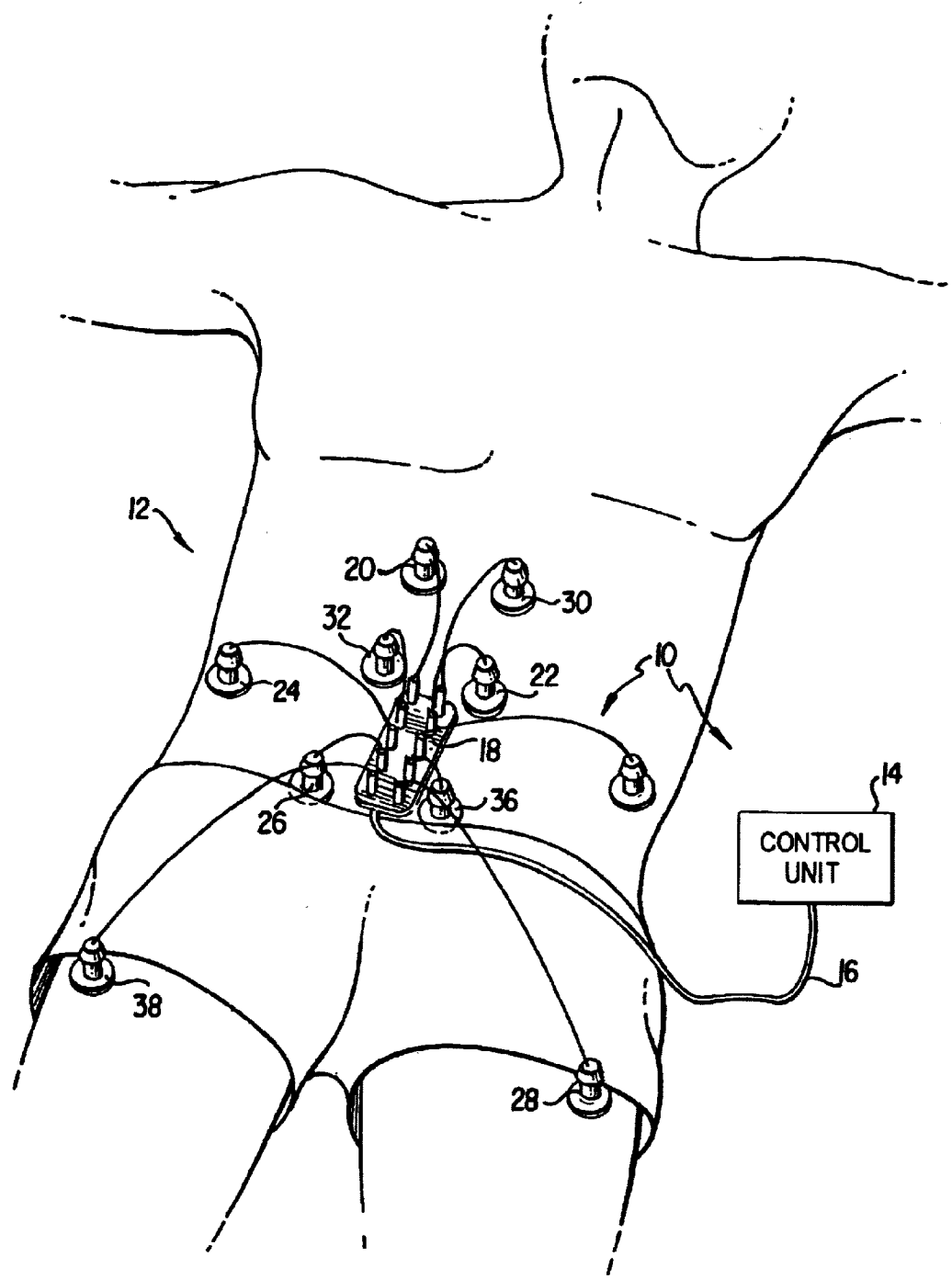
FIG. 1 shows a montage of electrodes and a control unit for treating low back pain of a patient with electrical therapy in accordance with an embodiment of the present invention.

FIG. 1 illustrates a system 10 for providing electrical therapy to a patient 12 in accordance with an embodiment of the invention. Here, the patient is being treated for low back pain.

The system 10 can include a plurality of electrodes or other electrical contact elements and a control unit 14. A first half of the electrodes including electrodes 20, 22, 24, 26, and 28 can form cathode electrodes, and a second half of the electrodes including electrodes 30, 32, 34, 36, and 38 can form corresponding anode electrodes. Each electrode can include a probe, such as a needle, which may be inserted into the patient's tissue for percutaneous therapy. Alternatively, each electrode can include a surface-mounted patch for transcutaneous therapy. In either embodiment, once the electrodes are placed as shown, a therapeutic electrical signal can be applied by the control unit 14 through a cable 16 and distributed between each cathode/anode electrode pair 20, 30; 22, 32; 24, 34; 26, 36; and 28, 38 by a tool tray 18. The number and placement of the electrodes and their designations as cathode or anode may be different in other embodiments.

In accordance with an embodiment of the invention, the control unit 14 can automatically vary the frequency of the electrical signal pulses applied to the electrodes over a comparatively wide range of frequencies. In one embodiment, the frequency of the electrical pulses can vary from a minimum frequency of at most about 20 Hz to a maximum frequency of at least about 40 Hz. By varying the frequency over a range, numerous therapeutic physiologic responses can result, in direct contrast to isolated physiologic responses obtained by conventional systems through the use of a single or limited number of frequencies. Still further, because each individual therapy patient has different physiologic response characteristics as a function of applied frequency, the automatically varying frequency of the electrical signal can be effective for a large patient population not withstanding their different physiologic response characteristics. Still further, the automatically varying frequency can eliminate the aforementioned trial and error and can permit non-physician personnel to apply the therapy to each patient in a uniform manner and with effective results.

Figure 2:
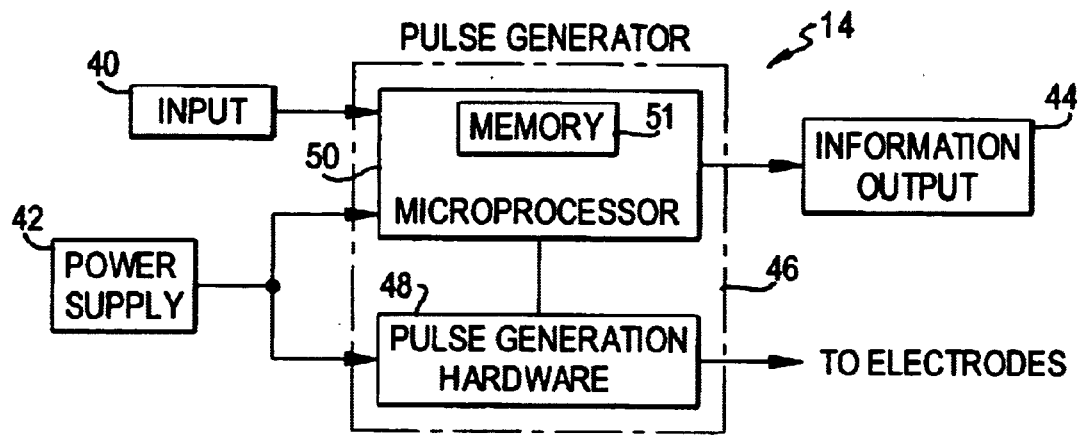
FIG. 2 is a schematic block diagram of the control unit of FIG. 1.

FIG. 2 schematically illustrates features of the control unit 14 in accordance with an embodiment of the invention. The control unit can include an input 40, a power supply 42, an information output 44, and a pulse generator 46. The pulse generator 46 can include pulse generation hardware 48 and a microprocessor 50. The microprocessor 50 can include a memory 51, or, alternatively, the memory 51 can be external to the microprocessor 50.

As described in greater detail below, the control unit 14 can provide an electrical signal that automatically varies in frequency over a comparatively broad range of frequencies. As will also be described below, the control unit 14 may compensate or adjust characteristics of the electrical signal depending on the frequency of the electrical signal. The input 40 can provide selection of the electric signal frequency range, the manner in which the frequency is automatically varied in the selected range, and the manner in which the electrical signal is compensated. The input 40 can include a keypad in one embodiment and can include other manual or automatic input devices in other embodiments.

The power supply 42 provides suitable operating voltage to the various active components of the control unit 14. It may be of a design well known in the art.

The information output 44 may be a liquid crystal display or the like. The information output 44 may be used to display the selected frequency range, the selected manner in which the frequency is automatically varied, and the selected manner in which the electrical signal is compensated with frequency.

Figure 4:
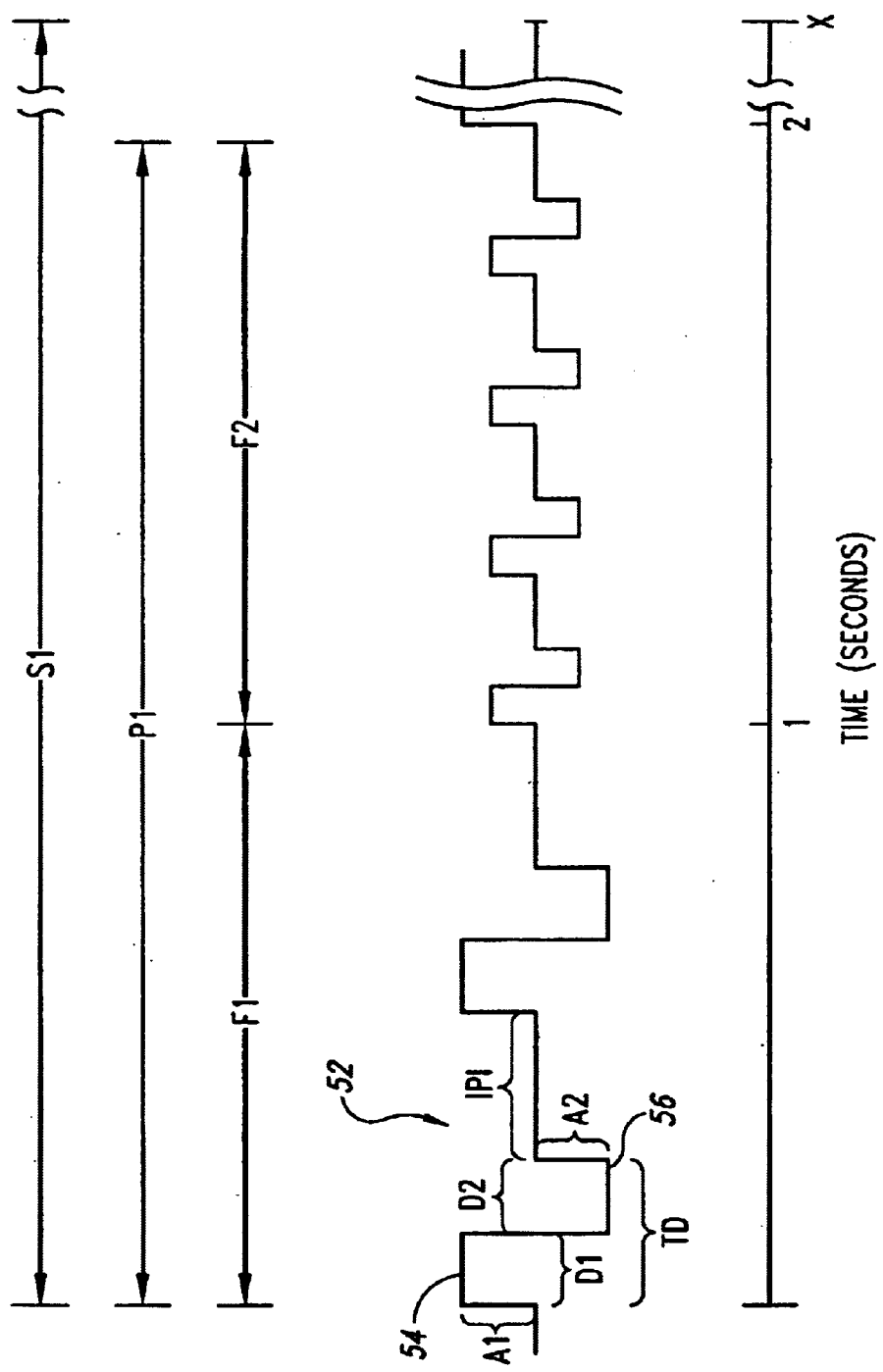
FIG. 4 is a waveform illustrating a therapy session including one complete cycle or period of an electrical signal which may be applied to the electrodes of FIG. 1 in accordance with an embodiment of the invention.

The pulse generation hardware 48 may be of the type well known in the art. It provides the electrical signal under the control or direction of the microprocessor 50. The electrical signal is can include a series of biphasic pulses 52 as shown in FIG. 4. Each biphasic pulse can include a consecutive pair of pulses, including a first pulse 54 of one polarity and a second pulse 56 of an opposite polarity. Alternatively, the first pulse 54 or the second pulse 56 can be eliminated, so that the pulses are of a single polarity. Each pulse 54 and 56 can have a duration D1 and D2, respectively. D1 and D2 can be on the order of 200 microseconds in one embodiment, or D1 and D2 can have other values in other embodiments. The durations D1 and D2 can be equal in one embodiment, or unequal in other embodiments. The durations D1 and D2 together define a total pulse duration TD which, as discussed below, may be varied with frequency as one manner of compensating the electrical signal.

Each of the pulses 54 and 56 also has a current amplitude A1 and A2, respectively. The amplitudes A1 and A2 may be different or equal, with a value of between about 2 and 5 milliamperes and a maximum value between about 10 and 15 milliamperes in one embodiment. As described below, the amplitudes A1 and A2 may be varied with frequency as a manner of compensating the electrical signal with frequency, in accordance with an embodiment of the invention.

The biphasic pulses are separated by an interpulse interval IPI. The IPI alone may be varied by the control unit 14 for automatically varying the frequency of the electrical signal. When the total pulse duration TD is varied to compensate the electrical signal, the IPI is then varied in concert with the TD to obtain the desired adjustments in the electrical signal frequency.

In the simplified example shown in FIG. 4, the electrical signal has a pulse frequency F1 of 2 Hz for one second and a frequency F2 of 4 Hz for the next second. This two-second pattern defines a cycle or period P1 which can be repeated over the course of a therapy session S1. In other embodiments, the frequency, amplitude, durations and periods can vary in other manners over the course of the session, as will be described in greater detail below. As will also be described below, it can be advantageous to have a period with a value of greater than 6 seconds.

Figure 3:
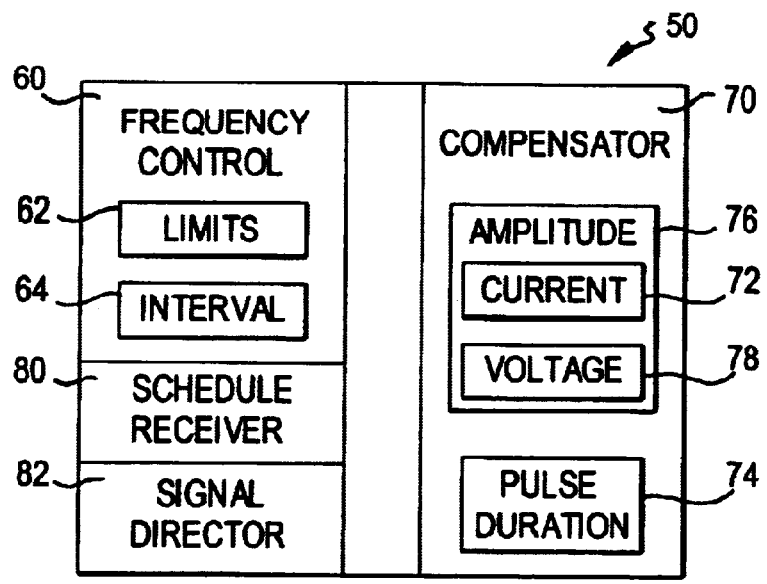
FIG. 3 is a more detailed schematic representation of a microprocessor of the control unit of FIG. 2.

FIG. 3 is a more detailed schematic illustration of the microprocessor 50 described above with reference to FIG. 2. In a conventional manner, the microprocessor executes operating instructions, which it can fetch from the memory 51 to provide its desired functionality in controlling the electrical signal applied to the electrodes. In doing so, the microprocessor 50 implements a plurality of functional stages, which may be divided into two groups of functional stages including frequency control stages 60 and compensator stages 70. The frequency control stages 60 can include a limits stage 62 and an interval control stage 64. The compensator stages 70 can include an amplitude control stage 72 and a pulse duration control stage 74. The amplitude control stage 72, as shown, can include substages including a current amplitude control stage 76 and a voltage amplitude control stage 78.

The limits stage 62, responsive to commands from the input 40, can set the frequency range of the electrical signal. The interval control stage 64 in turn varies the IPI automatically to automatically vary the frequency of the electrical signal. The manner in which the interval control stage 64 varies the frequency can be selectable from the input 40. For example, the frequency may be increased and decreased monotonically across the frequency range or varied randomly. The general frequency range previously referred to may be augmented so that, for example, the minimum frequency can be at most about 4 Hz while the maximum frequency can be at least 50 Hz. Alternatively, the minimum frequency can be at most 2 Hz or at most 4 Hz and the maximum frequency can be at least about 10 Hz, 15 Hz, 20 Hz or any value in between. In still further embodiments, the minimum frequency can be at most about 2 Hz while the maximum frequency can be at least about 100 Hz, or the minimum frequency can be at most about 2 Hz and the maximum frequency can be at most about 200 Hz.

The IPI between electrical pulses may be varied with each biphasic pulse or varied at less frequent intervals in a predetermined manner so that the IPI over a portion or multiple portions of the electrical signal is held constant. The IPI may be varied monotonically or randomly in a repeated manner. In one embodiment, the IPI is varied frequently enough so that a multitude of different frequencies, (for example, at least seven), are generated during a therapy session.

The compensator stage 70 can compensate the electrical signal as the frequency changes to maintain effective signal energy for each frequency of application. With a constant total duration (TD) and amplitude, the amount of applied electrical energy per unit time and consequently the perceived intensity of the stimulation will be directly related to frequency. Hence, higher frequencies will cause more energy per unit time to be applied to the recipient than will lower frequencies. To compensate for this, and to provide effective signal energy per unit time for each applied frequency, the compensator 70, under control of input 40, may adjust the current amplitude of the electrical signal as a function of frequency with stage 76, the voltage amplitude of the electrical signal as a function of frequency with stage 78, or the total pulse duration (TD) as a function of frequency with stage 74. In one aspect of this embodiment, the amplitude and TD can be varied in an inverse relation with frequency to maintain the amount of applied energy at an approximately constant level as the pulse frequency changes.

In any of the foregoing embodiments, the microprocessor can include a schedule receiver 80 and a signal director 82 that coordinate input to the frequency control 60 and the compensator 70 and output to the pulse generation hardware 48. For example, the schedule receiver can receive information (e.g., via the input 40) regarding the manner with which electrical pulses are to be scheduled during a treatment session. The signal director 82 can direct the pulse generation hardware 48 to emit electrical pulses in accordance with the received schedule.

Figure 5:
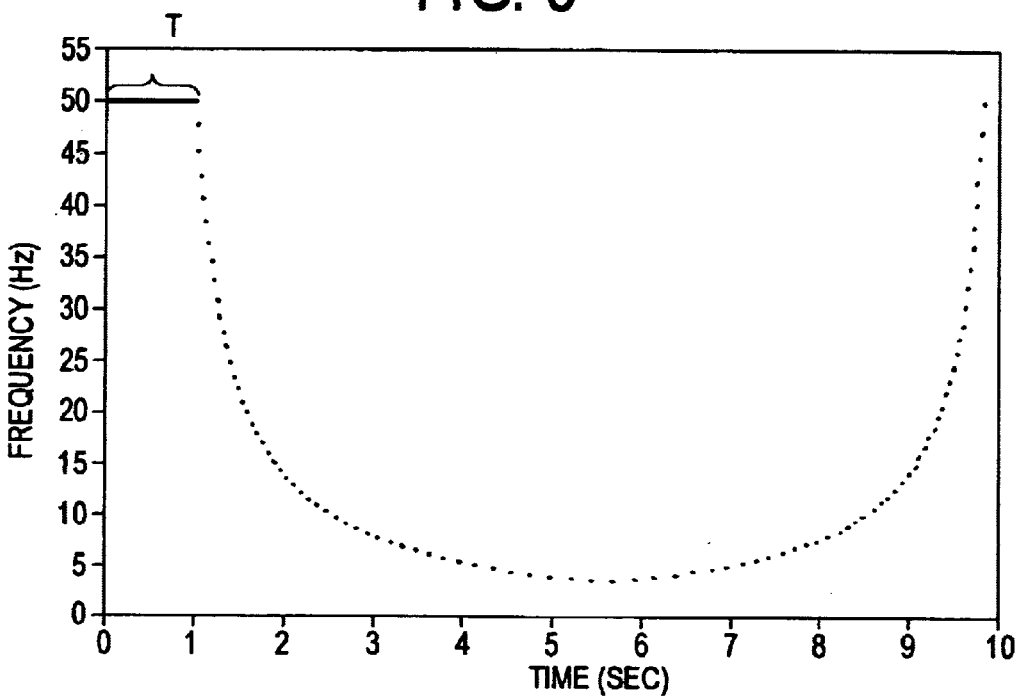
FIG. 5 is a plot of electrical signal frequency as a function of time illustrating the manner in which the frequency of the electrical signal may be varied in accordance with an embodiment of the present invention.

FIG. 5 illustrates a manner in which an electrical signal may be varied over time. It will be noted that during an initial time T the electrical signal frequency dwells or is held constant at an upper limit. This allows the recipient to feel a massage-like sensation for a brief period before the frequency begins to vary. Here, the frequency is decreased monotonically and then is increased monotonically. Preferably, at the end of the session, the frequency of the electrical signal pulses is once again held at the upper frequency limit for a few seconds so that the patient leaves with a positive impression.

Figure 6:
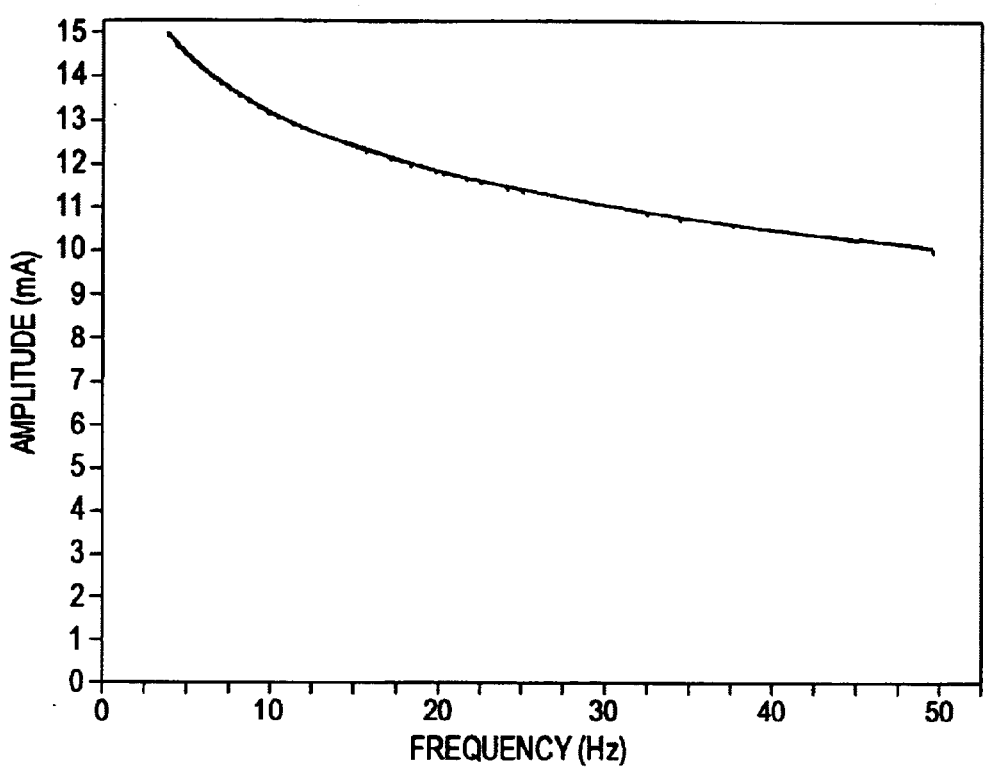
FIG. 6 is a plot illustrating the manner in which the electrical signal pulse amplitude may be varied with electrical signal frequency in accordance with an embodiment of the invention.

FIG. 6 illustrates how the pulse amplitude of the electrical signal represented in FIG. 5 may be adjusted with frequency. The relationship illustrated is adjustment in current in accordance with the formula:

$$I = C_1 - C_2 \log(F)$$

wherein, $C_1$ and $C_2$ are constants, and

F is the frequency of the electrical signal pulses.

Figure 7:
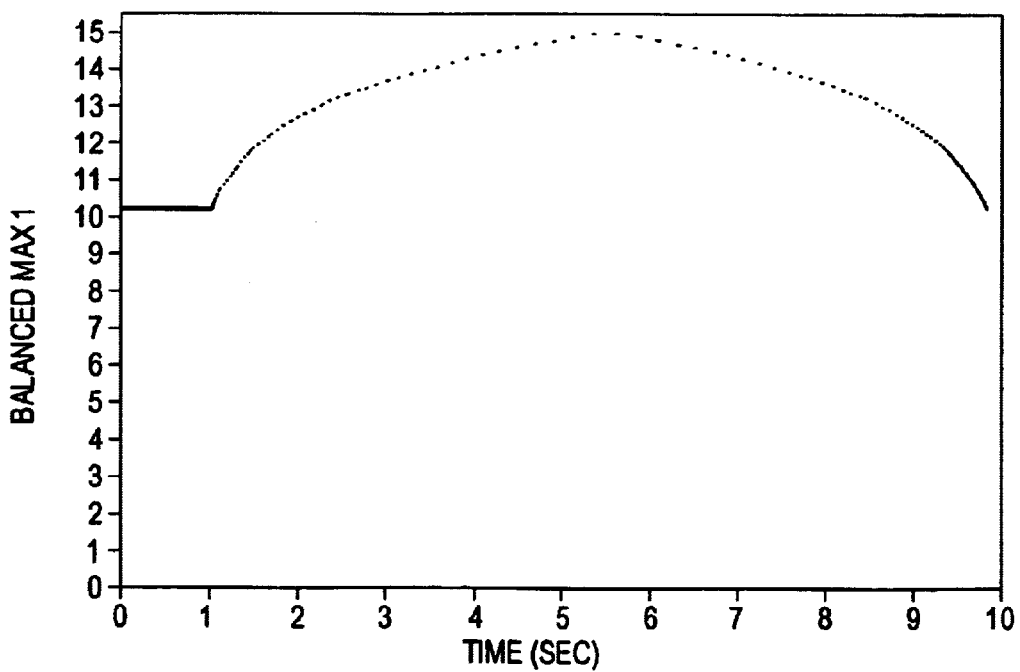
FIG. 7 is a plot illustrating the resulting electrical signal pulse amplitude as a function of time when the electrical signal pulse amplitude is varied with frequency as illustrated in FIG. 6.

The resulting adjusted current is illustrated in FIG. 7. It is of course understood that a therapy cycle generally exceeds 10 seconds and that the frequency and amplitude pattern illustrated in FIGS. 5 and 7 can be repeated until the therapy session is complete.

Figure 8:
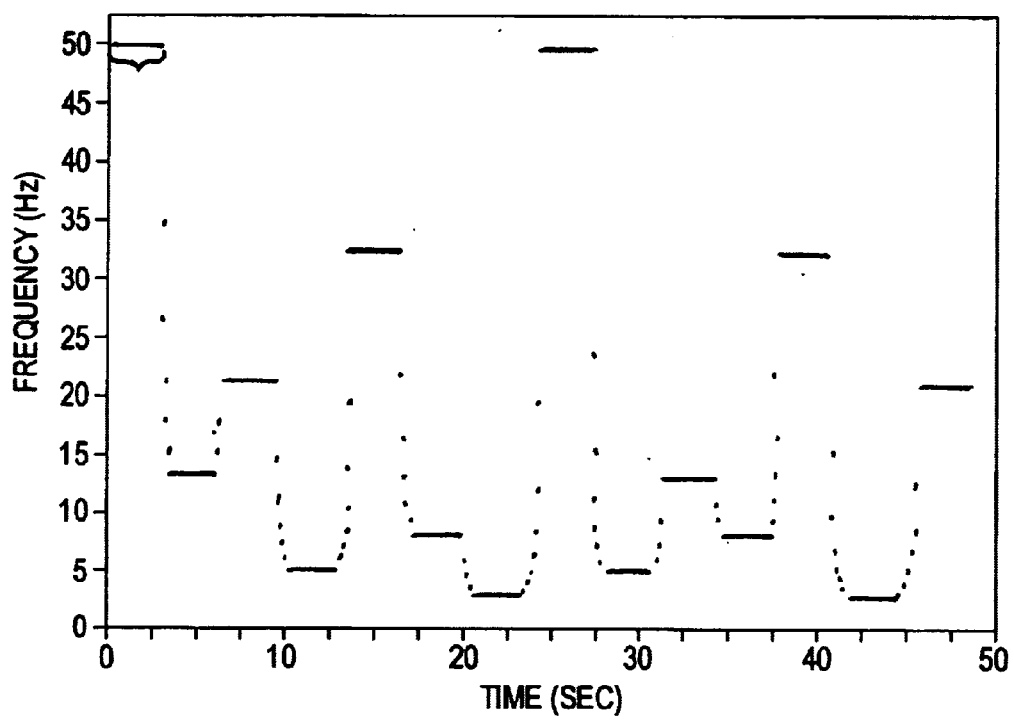
FIG. 8 is a plot illustrating the manner in which the electrical signal frequency may be randomly varied with time in accordance with another embodiment of the invention.

FIG. 8 shows another manner in which the frequency of the electrical signal may be varied over time. Again, the electrical signal dwells at the upper limit for an initial time T and then thereafter varies randomly within the selected frequency range. With each adjustment in frequency, the frequency, and hence the IPI is held constant for a few seconds. During each adjustment in frequency, the IPI varies monotonically between the previously selected frequency and the newly selected frequency.

Figure 9:
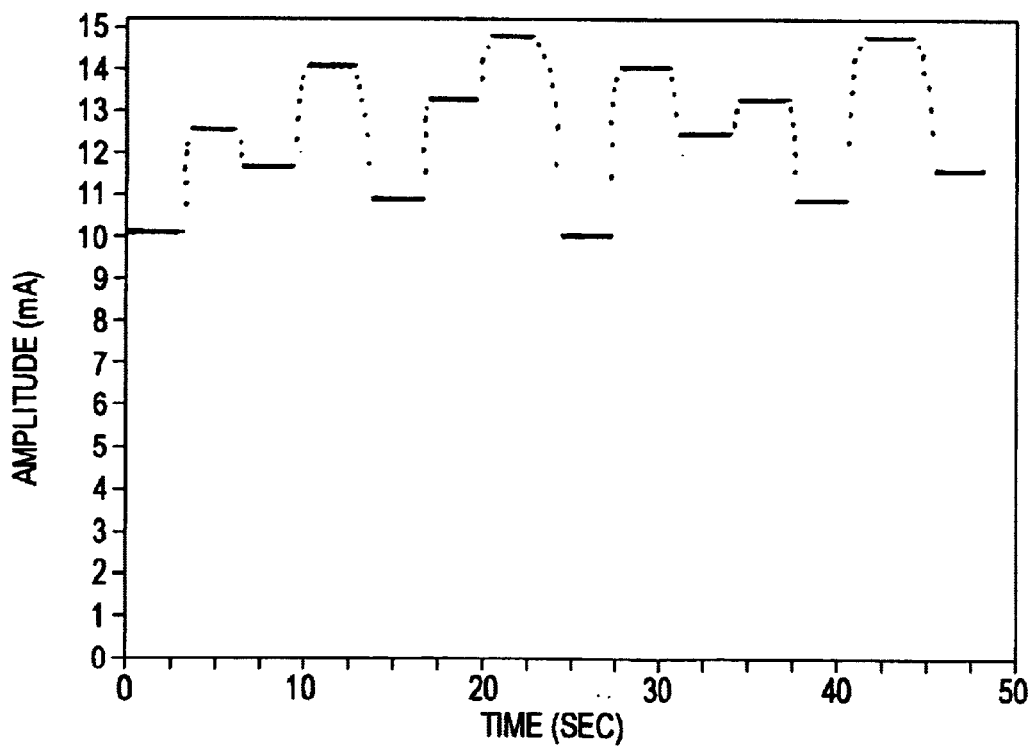
FIG. 9 is a plot illustrating the resulting electrical signal pulse amplitude as a function of time when the electrical signal amplitude is varied with frequency as illustrated in FIG. 6.

FIG. 9 shows the current amplitude versus time for the electrical signal represented in FIG. 8 wherein the current is adjusted in accordance with the relationship to frequency as described with respect to FIG. 6. Either the current amplitude or the voltage amplitude may be adjusted in this manner.

Figure 10:
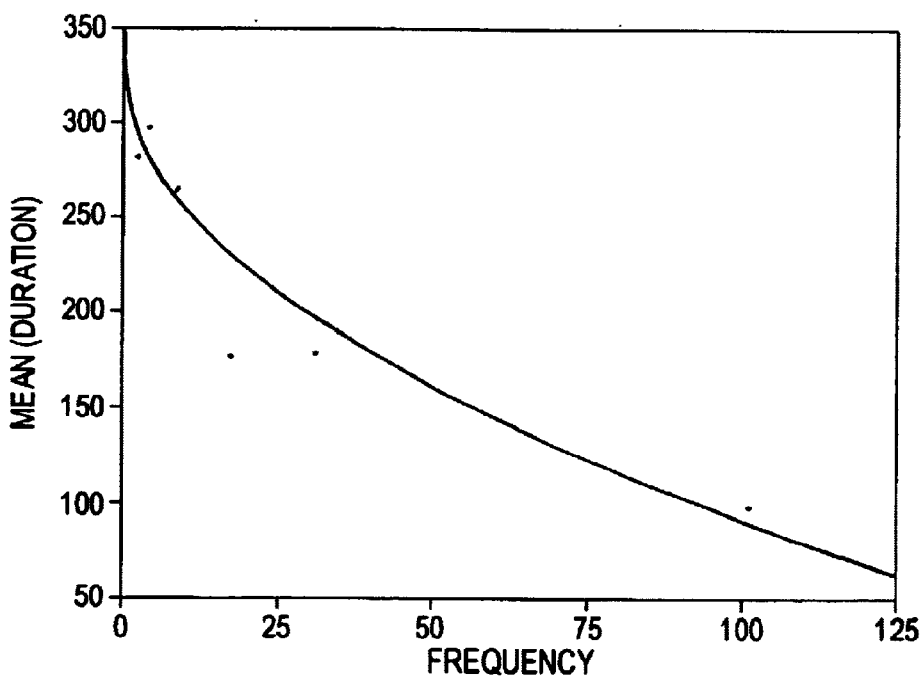
FIG. 10 is a plot illustrating the manner in which the electrical signal pulse width may be varied with frequency in accordance with another embodiment of the invention.

FIG. 10 shows the compensation made to the electrical signal represented in FIG. 5 wherein the total pulse duration (TD) (instead of the amplitude) is varied with frequency. In one embodiment, the relationship for adjustment in total pulse duration can be represented with the formula:

$$TD = C_1 - C_2 \sqrt{F}$$

wherein, $C_1$ and $C_2$ are constants, and

F is the frequency of the electrical signal pulses.

As those skilled in the art will appreciate, both amplitude and duration may be varied together to achieve the desired electrical signal compensation with frequency.

Figure 11:
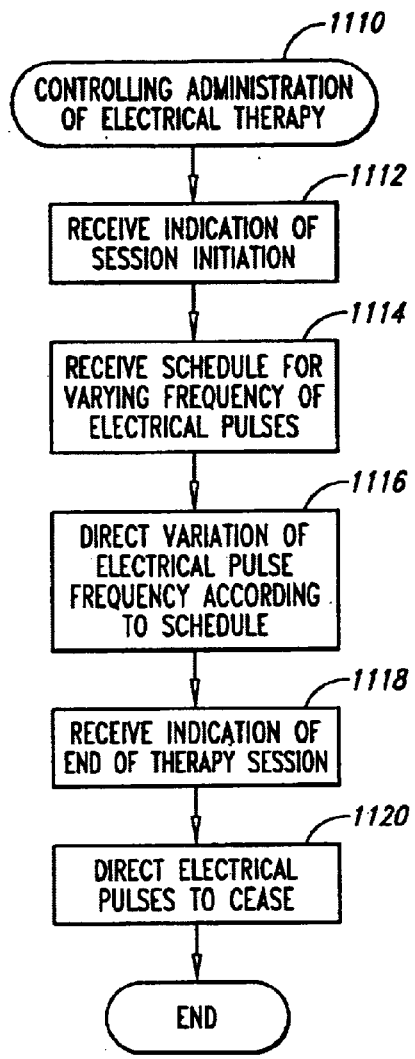
FIG. 11 is a flow diagram illustrating a process for controlling administration of electrical therapy in accordance with another embodiment of the invention.

Many of the operations described above with reference to the foregoing embodiments and described below with respect to further embodiments can be performed manually. Alternatively, these processes can be performed automatically, for example, by a computer-based system (or microprocessor-based system), such as the one described above with reference to FIG. 2. Accordingly, many of the operations can be performed as steps, routines, or subroutines of a computer program. For example, as shown in FIG. 11, a process 1110 for controlling the administration of electrical therapy can include receiving an indication of the initiation of a therapy session (step 1112). In step 1114, the process can include receiving a schedule for varying the frequency of electrical pulses provided to a patient or recipient during the course of the session. In step 1116, the process can include directing the variation of the electrical pulse frequency according to the schedule received in step 1114. In step 1118, the process can include receiving an indication that the therapy session is at an end, and in 1120, the process can include directing the electrical pulses to cease.

In one aspect of an embodiment described above with reference to FIG. 11, the process steps can be performed by computer software and the session initiation and termination indications (steps 1112 and 1118) can be manually input to the program by a practitioner operating the input 40 (FIG. 2). Alternatively, these indications can be retrieved by the program from a database. Similarly, the step of receiving a schedule for varying the frequency of electrical pulses (step 1114) can include receiving a schedule that is input manually by a practitioner, or alternatively, the schedule can be retrieved by the software program from a database. The database can be stored in local memory (such as the memory 51 described above with reference to FIG. 2) or remote memory. The database can be stored on any computer-readable medium, such as, but not limited to, magnetic and optically readable and removable computer disks, as well as media distributed electronically over the Internet or over other networks (including wireless networks).

In any of these embodiments, the software performing the steps of directing the variation of electrical pulse frequency according to the schedule (step 1116) and directing the electrical pulses to cease (step 1120) can be operatively coupled to a pulse generator (such as was described above with reference to FIG. 2) to control the pulses delivered by the generator to the recipient.

Figure 12:
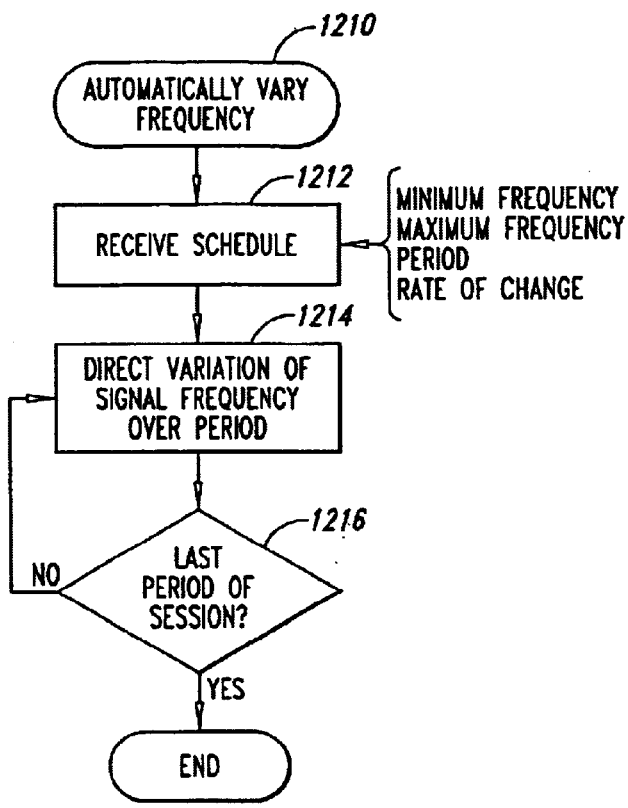
FIG. 12 is a flow diagram illustrating a process for automatically varying the frequency with which electrical pulses are administered to a recipient in accordance with another embodiment of the invention.

FIG. 12 is a flow diagram of a process 1210 for automatically varying the frequency with which electrical pulses are delivered to a recipient. In 1212, the process can include receiving a schedule for varying the frequency. The schedule can include a minimum frequency value, a maximum frequency value, pulse durations and/or IPIs for each frequency, a period over which the frequency changes from the minimum value to the maximum value and back, and a rate at which the frequency changes from the minimum value to the maximum value and back. In step 1214, the process can include directing the variation in signal frequency over the period. In step 1216, the process determines whether the period just completed is the last period of the session. If the just-completed period is not the last period, the process returns to step 1214 to direct the variation of the signal frequency over the next period. Step 1214 is repeated until the session ends.

Figure 13:
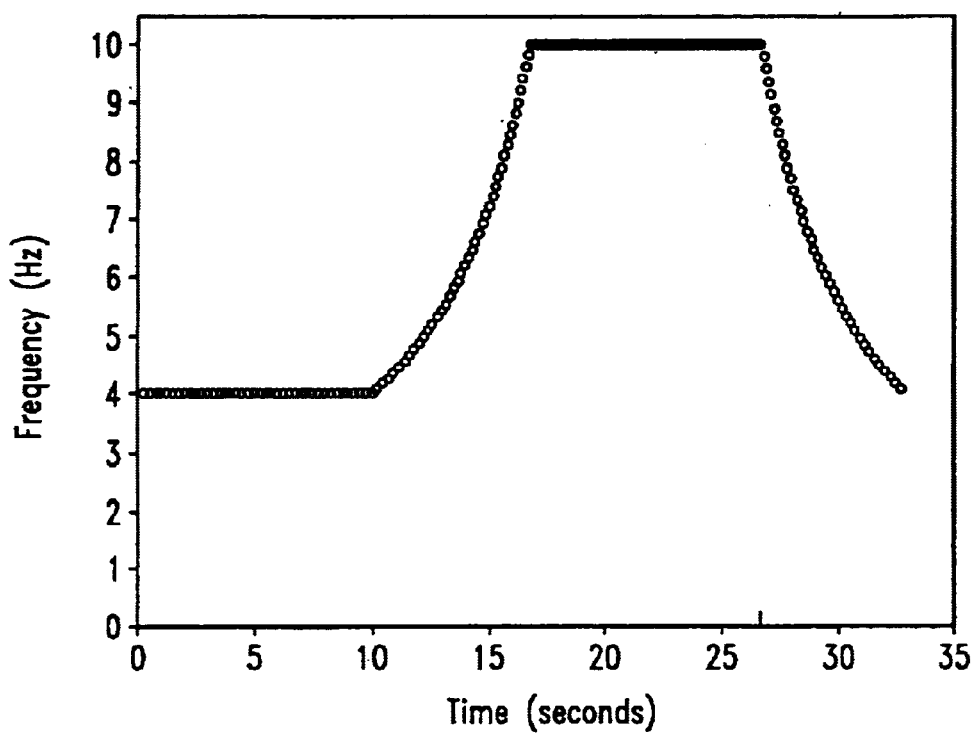
FIG. 13 is a plot illustrating the manner in which the frequency of electrical pulses delivered to a recipient can vary in accordance with an embodiment of the invention.

In one aspect of this embodiment, the frequency of the electrical pulses delivered to the recipient can vary between the minimum and maximum frequencies described above with reference to FIG. 3. Alternatively, the frequency of the electrical pulses can vary from a minimum frequency of about 4 Hz to a maximum frequency of about 10 Hz, as shown in the plot of FIG. 13. In a further aspect of this embodiment, the electrical pulses can be delivered to the recipient at the minimum frequency for an initial interval of about ten seconds. The frequency can then be gradually increased to the maximum frequency of about 10 Hz over a time interval of about seven seconds. The electrical pulses can be delivered at the maximum frequency for a time interval of about ten seconds, and the frequency can then be decreased back to the minimum frequency over a time interval of about 6 seconds. Accordingly, the period of the frequency schedule shown in FIG. 13 is about 33 seconds.

Figure 14:
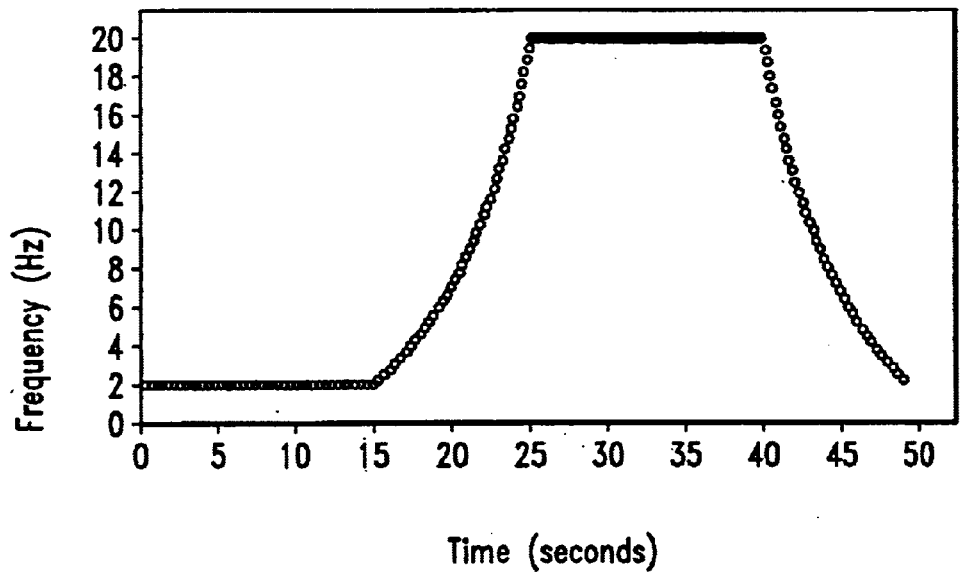
FIG. 14 is a flow diagram illustrating a process for tracking treatment periods in accordance with another embodiment of the invention.

In an alternative embodiment (shown in FIG. 14), the frequency of electrical pulses can vary between about 2 Hz and about 20 Hz over a period of about 50 seconds. Alternatively, the length of the period can have other values, for example, a value greater than 6 seconds, up to and including about 2 minutes. In one particular embodiment, the period can have a value of about 10 seconds. The maximum frequency (which can range from about 10 Hz to about 20 Hz in one embodiment) can be low enough to trigger the release of endorphins in the recipient, which can have a therapeutic benefit and can provide a positive sensation for the recipient. In a further alternate embodiment, the frequency does not remain constant at the beginning and end of each period, but changes constantly during the period.

In any of the embodiments described above with reference to FIGS. 1–14, the electrical pulses can be delivered in a manner that is repeated from one period to the next until the therapy session is complete. Alternatively, the duration of the periods and/or other aspects of the schedule for each period can change throughout the course of the session, as will be described in greater detail below.

FIG. 15 graphically illustrates a schedule for a 30-minute session during which the maximum and/or minimum frequency of electrical pulses delivered to the recipient during a given period varies over the course of the session, in accordance with an embodiment of the invention. In one aspect of this embodiment, the frequency is constant at the beginning and the end of the session. During an intermediate portion of the session, the frequency varies between a minimum frequency 1512a and a maximum frequency 1510. The difference between the minimum frequency 1512a and the maximum frequency 1510 can increase until the midpoint of the session (at 15 minutes in the example shown in FIG. 15), then decrease until the frequency is again constant toward the end of the session.

In the embodiment shown in FIG. 15, the electrical pulse frequency cycles between a constant minimum frequency 1512a of about 4 Hz and a maximum frequency 1510 that increases up to 15 Hz, then decreases. At 12.5 minutes into the therapy session, the electrical pulse frequency cycles between 4 Hz and 10 Hz. The manner in which the frequency changes from minimum to maximum at this point in the session was described above and shown in FIG. 13. The electrical pulse frequency can cycle between minimum and maximum values in a similar fashion at other points in the session.

In one aspect of this embodiment, the frequency can cycle between the maximum frequency 1510 and the constant minimum frequency 1512a. Alternatively, the frequency can cycle between the maximum frequency 1510 and a minimum frequency 1512b that first decreases and then increases. In another embodiment, the frequency can cycle between the maximum frequency 1510 and a minimum frequency 1512c that first increases then decreases.

In other embodiments, the frequency can vary over the course of the session in accordance with other schedules. For example, the minimum frequency and maximum frequency may not be the same at the beginning and end of the session, and may or may not be the same during other portions of the session. The minimum and maximum frequencies can be greater than or less than the values shown in FIG. 15, and the rates at which the minimum and maximum frequencies change can be different than is shown in FIG. 15. In any of these embodiments, the manner in which the frequency changes can be selected based on the effect or expected effect on a patient or group of patients.

FIG. 16 is a flow chart schematically illustrating a process 1610 for tracking electrical stimulation periods during the course of a therapy session. In step 1612, the process includes receiving the duration of a given period. In step 1614, the process includes receiving a frequency change schedule for the given period. For example, the frequency change schedule can be generally similar to any of the schedules described above. In step 1616, the process includes directing the frequency variation of electrical pulses over the given period. In step 1618, the process determines whether or not the just-completed period is the last period of the session. If not, steps 1612–1618 are repeated until the end of the session.

In one aspect of this embodiment, each of the periods throughout the session can have the same duration and the same frequency change schedule. For example, each period can last 33 seconds, as described above with reference to FIG. 13. Alternatively, the periods can have a different length of time, for example, any length of time greater than 6 seconds and less than about 120 seconds. In one particular embodiment, the period can have a value of at least 10 seconds. An advantage of a period having a value greater than 6 seconds is that the recipient may be more likely to relax during treatment because the rate at which the frequency changes is lower than for some conventional devices that change the frequency over a period of 6 seconds or less.

In still another alternative embodiment, the length of the period, the minimum and maximum frequencies attained during the period, the rate with which the frequencies are changed during the period, and/or the amplitude of the current and/or voltage administered to the recipient during the period may be changed over the course of a given session. For example, the length of each period may be selected in accordance with the recipient's state of mind or expected state of mind. Recipients who may be anxious toward the beginning of the session can accordingly receive therapy having initially short periods that gradually lengthen over the course of the session as the recipient relaxes. Alternatively, the periods can initially be relatively long to counteract the recipient's initial anxiety.

In a further aspect of this embodiment, the treatment process can include a biofeedback loop that automatically changes the length of the period (or other aspects of the treatment, such as pulse frequency) in accordance with changes in the recipient's physical state. For example, a signal indicating the recipient's respiration rate, heart rate, brain waves and/or diaphoretic response can be operatively coupled to the microprocessor 50 (FIG. 2) in a conventional manner (for example, via the input 40) to control or affect the characteristics of the electrical pulses.

FIG. 17 is a flow chart illustrating a process 1710 for varying the schedule of electrical pulses administered to the recipient based on the duration of the session during which the pulses will be administered. In step 1712, the process includes receiving a session time duration and in step 1714, the process includes determining the schedule according to which the frequency and/or other characteristics (such as the duration, amplitude and/or interpulse interval) will change during the course of the session. In one embodiment, the changes can occur in a gradual manner, for example, by a series of closely spaced step changes. Changes in frequency can be compensated for by changes in pulse total duration and/or amplitude, as described above with reference to FIGS. 7 and 10. The schedule can be determined by a formula, a table lookup, an input from a practitioner, and/or by other sources. In any of these embodiments, the schedule selected for a particular session time is selected based on the session time. Accordingly, the characteristics of the schedule are correlated with the length of time available for a particular session. The process can further include directing the variation of the electrical pulse signal in accordance with the schedule (step 1716). In step 1718, the process can determine whether the just-completed session is the last session to be conducted. If further sessions are to be conducted (for example, on other recipients), steps 1712–1718 are repeated until all sessions have been complete.

Figure 18:
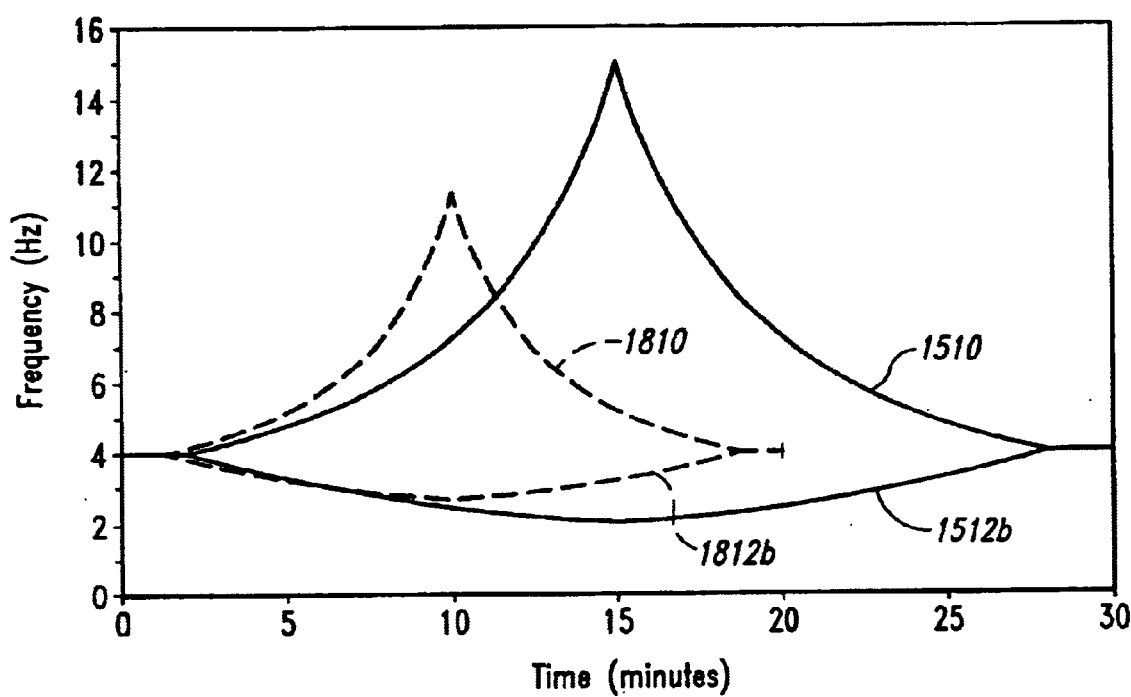
FIG. 18 is a plot illustrating frequency change schedules for two sessions in accordance with yet another embodiment of the invention.

FIG. 18 graphically compares frequency change schedules for two sessions in accordance with an embodiment of the invention. For purposes of comparison, the maximum frequency 1510 and minimum frequency 1512b schedules described above with reference to FIG. 15 for a 30-minute session are shown again in FIG. 18. Also shown in FIG. 18 are schedules for a maximum frequency 1810 and a minimum frequency 1812*b* for a 20-minute session. In one aspect of this embodiment, the peak maximum frequency 1810 can be lower than the peak maximum frequency 1510, and the lowest minimum frequency 1812*b* can be greater than the lowest minimum frequency 1512*b*. In a further aspect of this embodiment, the length of time during which the frequency remains constant (at the beginning and end of the session) can be less for the 20-minute session than for the 30-minute session.

In other embodiments, other aspects of the treatment schedule can be different for sessions having different session lengths. For example, the schedules for shorter sessions can be scaled linearly directly from the schedules for longer sessions (as shown in FIG. 18) or, the sessions can differ in non-linear fashions. In one specific example, the schedule can begin with the peak maximum frequency and lowest minimum frequency and end with the maximum and minimum frequencies the same. In other embodiments, the schedules can have other arrangements. For example, the period over which the frequency varies from maximum to minimum in a 20-minute session can vary from about 10 seconds to about 30 seconds over the course of the session, and the period over which the frequency varies from maximum to minimum can vary from about 10 seconds to about 120 seconds for a 45-minute session.

As may thus be seen from the foregoing, embodiments of the invention provide new and improved systems and methods for treating a patient with electrical therapy. In accordance with certain embodiments of the invention, the frequency of the applied electrical signal can be automatically varied. Thus, an aspect of the invention can eliminate adjusting pulse frequencies for a given patient by trial and error. Further, a broad range of caregivers may use the system with minimal medical training and provide effective therapy for a large patient population.

In addition, embodiments of the invention can overcome the problem with patients becoming physiologically adapted to single or a limited number of frequencies. Still further, in addition to overcoming physiologic adaptation, embodiments of the present invention can provide a therapy that is not perceived as monotonous, a common patient perception when receiving a constant stimulus for a typical treatment session of 30 minutes.

While particular embodiments of the present invention have been shown and described, modifications may be made, and it is therefore intended to cover in the appended claims all such changes and modifications which fall within the true spirit and scope of the invention.

What is claimed is:

1. A method for delivering electrical therapy to a recipient, comprising:

coupling an electrode to the recipient;

applying electrical pulses to the electrode;

varying a frequency of the electrical pulses over a first range of frequencies for a first period of time greater than 6 seconds during a therapy session;

varying the frequency of the electrical pulses over a second range of frequencies for a second period of time approximately the same as the first period of time during the therapy session;

wherein varying the frequency over the first range of frequencies includes gradually changing the frequency from about 4 Hz to about 10 Hz over an approximately 7 second interval, and wherein the method further comprises:

maintaining the frequency at about 4 Hz for about 10 seconds before changing the frequency from about 4 Hz to about 10 Hz;

maintaining the frequency at about 10 Hz for about 10 seconds after changing the frequency from about 4 Hz to about 10 Hz; and changing the frequency from about 10 Hz to about 4 Hz over an approximately 6 second interval.

2. A method for delivering electrical therapy to a recipient, comprising:

coupling an electrode to the recipient;

applying electrical pulses to the electrode;

varying a frequency of the electrical pulses over a first range of frequencies for a first period of time greater than 6 seconds during a therapy session;

varying the frequency of the electrical pulses over a second range of frequencies for a second period of time approximately the same as the first period of time during the therapy session;

wherein varying a frequency of the electrical pulses over a first range includes varying a frequency from a first minimum value to a first maximum value, and wherein varying the frequency of the electrical pulses over a second range includes varying a frequency from a second minimum value to a second maximum value, with the first minimum value being different than the second minimum value, and/or the first maximum value being different than the second maximum value;

maintaining the frequency at a first value before changing from the first value to a second value;

maintaining the frequency at the second value after changing from the first value to the second value; and changing the frequency from the second value to the first value after maintaining the frequency at the second value.

3. A method for delivering electrical therapy to a recipient, comprising:

coupling an electrode to the recipient;

applying electrical pulses to the electrode;

varying a frequency of the electrical pulses over a first range of frequencies for a first period of time greater than 6 seconds during a therapy session wherein varying the frequency over the first range includes maintaining the frequency at a first value over a first time interval, changing the frequency from the first value to a second value over a second time interval, maintaining the frequency at the second value over a third time interval, and changing the frequency from the second value to the first value over a fourth time interval;

varying the frequency of the electrical pulses over a second range of frequencies for a second period of time approximately the same as the first period of time during the therapy session;

wherein varying a frequency of the electrical pulses over a first range includes varying a frequency from a first minimum value to a first maximum value, and wherein varying the frequency of the electrical pulses over a second range includes varying a frequency from a second minimum value to a second maximum value, with the first minimum value being different than the second minimum value. and/or the first maximum value being different than the second maximum value.

4. A method for delivering electrical therapy to a recipient, comprising:

coupling an electrode to the recipient;

applying electrical pulses to the electrode;

varying a frequency of the electrical pulses over a first range of frequencies for a first period of time greater than 6 seconds during a therapy session;

varying the frequency of the electrical pulses over a second range of frequencies for a second period of time approximately the same as the first period of time during the therapy session;

receiving a signal from the recipient; and automatically adjusting the frequency of the electrical pulses in response to the signal received from the recipient, the signal including at least one of an electrical signal indicative of muscular activity, a temperature signal, and a diaphoretic signal, and a respiratory signal.

5. A method for delivering electrical therapy to a recipient, comprising:

coupling an electrode to the recipient;

applying electrical pulses to the electrode;

varying a frequency of the electrical pulses over a first range of frequencies for a first time period during a therapy session;

varying the frequency of the electrical pulses over a second range of frequencies for a second time period different than the first time period during the therapy session;

receiving a signal from the recipient; and automatically adjusting the frequency of the electrical pulses in response to the signal received from the recipient, the signal including at least one of an electrical signal indicative of muscular activity, a temperature signal, a diaphoretic signal, and a respiratory signal.

* * * * *